United States Patent
Priestley (12)

(10) Patent No.: US 6,317,209 B1
(45) Date of Patent: Nov. 13, 2001

(54) AUTOMATED SYSTEM FOR MEASUREMENT OF AN OPTICAL PROPERTY

(75) Inventor: Richard S. Priestley, Corning, NY (US)

(73) Assignee: Corning Incorporated, Corning, NY (US)

(*) Notice: Subject to any disclaimer, the term of this patent is extended or adjusted under 35 U.S.C. 154(b) by 0 days.

(21) Appl. No.: 09/458,561

(22) Filed: Dec. 9, 1999

(51) Int. Cl.[7] ........................................ G01J 4/00
(52) U.S. Cl. ............................. 356/365; 356/426
(58) Field of Search .................... 356/364, 365, 356/369, 426, 445, 446

(56) References Cited

U.S. PATENT DOCUMENTS

| | | | | |
|---|---|---|---|---|
| 3,811,775 | * | 5/1974 | Abu-Saud | 356/365 |
| 4,626,100 | * | 12/1986 | Johnson | 356/365 |
| 5,028,774 | * | 7/1991 | Yoshizawa et al. | 356/369 |
| 5,257,092 | | 10/1993 | Noguchi et al. | 356/367 |
| 5,587,793 | | 12/1996 | Nakai et al. | 356/367 |
| 6,025,906 | * | 2/2000 | Hepburn et al. | 356/426 |

FOREIGN PATENT DOCUMENTS

| | | | |
|---|---|---|---|
| 1 067 096 | 1/2001 | (EP) | C03C/3/06 |
| 63-82345 | 9/1988 | (JP) | G01N/21/23 |
| 02159540 | 12/1998 | (JP) | G01N/21/23 |

OTHER PUBLICATIONS

Baoliang Wang & Patrick M. Troccolo, Measurement of Residual Birefringence In Photomask Blanks, 19th Annual BACUS Symposium on Photomask Technology, Monterey, Calif, Sep. 15–17, 1999, SPIE vol. 3873.

* cited by examiner

Primary Examiner—F. L. Evans
Assistant Examiner—Zandra V. Smith
(74) Attorney, Agent, or Firm—Edward F. Murphy

(57) ABSTRACT

An apparatus for making automated measurements of an optical property of a sample includes a first stage which is movable along a predetermined line, a second stage for holding the sample, and a third stage which is movable along a predetermined line, correspondingly to the motion of the first stage. A light source is mounted on the first stage, and a light detector is mounted on the third stage. The second stage rotates the sample to a selected rotary position. The apparatus also includes a controller for coordinating movement of the first, second, and third stages such that the light source, the sample, and the light detector are optically aligned.

13 Claims, 4 Drawing Sheets

AUTOMATED SYSTEM FOR MEASUREMENT OF AN OPTICAL PROPERTY

BACKGROUND OF THE INVENTION

1. Technical Field

The invention relates generally to systems for measuring birefringence or other optical property, e.g., transmission, of a sample of material.

2. Background Art

Birefringence, or double refraction, is a phenomenon that occurs in materials characterized by two indices of refraction. Typically, birefringent materials are optically anisotropic substances, e.g., calcite and quartz. Although, some isotropic materials, e.g., glass and plastic, become birefringent when subjected to stress. When a beam of light enters a birefringent material, the beam splits into two polarized rays traveling with different velocities, corresponding to two different angles of refraction. One ray, called an ordinary ray, is characterized by an index of refraction that is the same in all directions. The second ray, called an extraordinary ray, travels with different speeds in different directions and hence is characterized by an index of refraction that varies with the direction of propagation. If the light entering the birefringent material is unpolarized or linearly polarized, the ordinary and extraordinary rays will have the same velocity along one direction, called the optic axis. The ordinary and extraordinary rays recombine upon exiting the material.

Birefringent materials can change the polarization state of a light passing through them. Therefore, the ability to accurately determine the birefringence of a sample is important, especially in high performance optics, e.g., ophthalmic lenses, laser optics, and optical fibers, where a change in the polarization state of light can cause dramatic changes in optical performance. When a linearly polarized light passes through a birefringent sample, the sample rotates the direction of polarization through some angle. By measuring this angle of rotation, the birefringence of the sample, i.e., the difference between the highest and lowest indices of refraction of the sample, can be determined. Typically, the sample is placed between two crossed linear polarizers. The birefringence at a given point about the cross section of the sample is then determined by measuring the angular position, with respect to the first linear polarizer, at which the light emerging from the sample is extinguished as it passes through the second linear polarizer.

Various other methods are known for determining birefringence. One example of a known method is disclosed in U.S. Pat. No. 5,257,092 issued to Noguchi et al. As shown in FIG. 1, an optical source unit 2 emits a linearly polarized light beam, which passes through a quarter-wave plate 4. The quarter-wave plate 4 converts the beam emitted by the optical source 2 to circularly polarized light, which then passes through the birefringent sample 6, where the light emerges elliptically polarized. This emergent light then passes through a second quarter-wave plate 8 which converts the light to near-linear polarized light. The light then passes through a rotatable analyzer 10. Birefringence is determined by measuring the angle of the analyzer 10 with respect to the source 2 at which light is extinguished. The method disclosed by this patent uses circularly polarized light rather than linearly polarized light because, in the samples used, birefringence had to be measured in all directions. If linearly polarized light is used, there inherently will be a direction in which no birefringence occurs, i.e., the optic axis.

Another example of a method for measuring birefringence is disclosed in U.S. Pat. No. 5,587,793 issued to Nakai et al. As illustrated in FIG. 2, a sample 12 is placed between a circular polarizer 14 and a circular analyzer 16 and arranged in an optical path between a light source 18 and an optical receiver 20. The circular polarizer 14 is a combination of a polarizer 22 and a quarter-wave plate 24, and the circular analyzer 16 is a combination of a quarter-wave plate 26 and an analyzer 28. The circular analyzer 16 is arranged in a crossed Nicols fashion with respect to the circular polarizer. A crossed Nicols fashion refers to the arrangement of the polarizers such that their polarization axes are set 90 degrees from one another. In this method, monochromatic parallel beams emitted from the light source 18 are converted into circularly polarized light by the circular polarizer 22 and projected onto sample 12. The light beams then pass through the circular analyzer 16 to be detected by the optical receiver 20.

The birefringence of the sample may vary from location to location across the sample. Thus, in order to describe the birefringence of a sample, birefringence at a number of points along or distributed on the surface of the sample is measured. One procedure used in industry includes taking a measurement at one position on the cross section of a sample and then manually moving the sample e.g., by using a lab jack, so that the measurement is made at another test point on the cross section. The measurements are repeated at numerous test points about the cross section of the sample to generate a birefringence map. Because mapping requires a large number of points, mapping the sample manually is a difficult and time-consuming task. In some cases, the actual measurement is also performed manually, with the operator having to determine the actual angle of light extinction. Therefore, the accuracy of these measurements can fluctuate from operator to operator.

SUMMARY OF THE INVENTION

One aspect of the invention is an apparatus for making automated measurements of an optical property of a sample. The apparatus comprises a first stage which is movable along a predetermined line, a second stage for holding the sample, and a third stage which is movable along a predetermined line, correspondingly to the motion of the first stage. A light source is mounted on the first stage, and a light detector is mounted on the third stage. The second stage rotates the sample to a selected rotary position. The apparatus further comprises a controller for coordinating movement of the first, second, and third stages such that the light source, the sample, and the light detector are optically aligned.

Other aspects and advantages of the invention will be apparent from the following description and the appended claims.

DETAILED DESCRIPTION OF THE INVENTION

Figure 1:
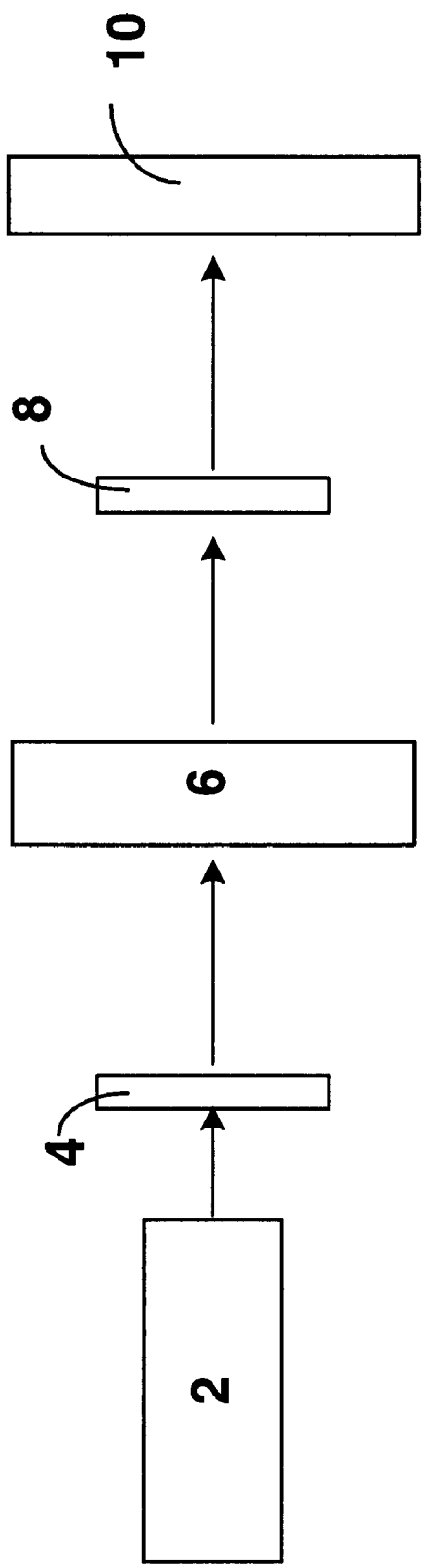
FIG. 1 shows a prior art system for obtaining birefringence of a material.
Figure 2:
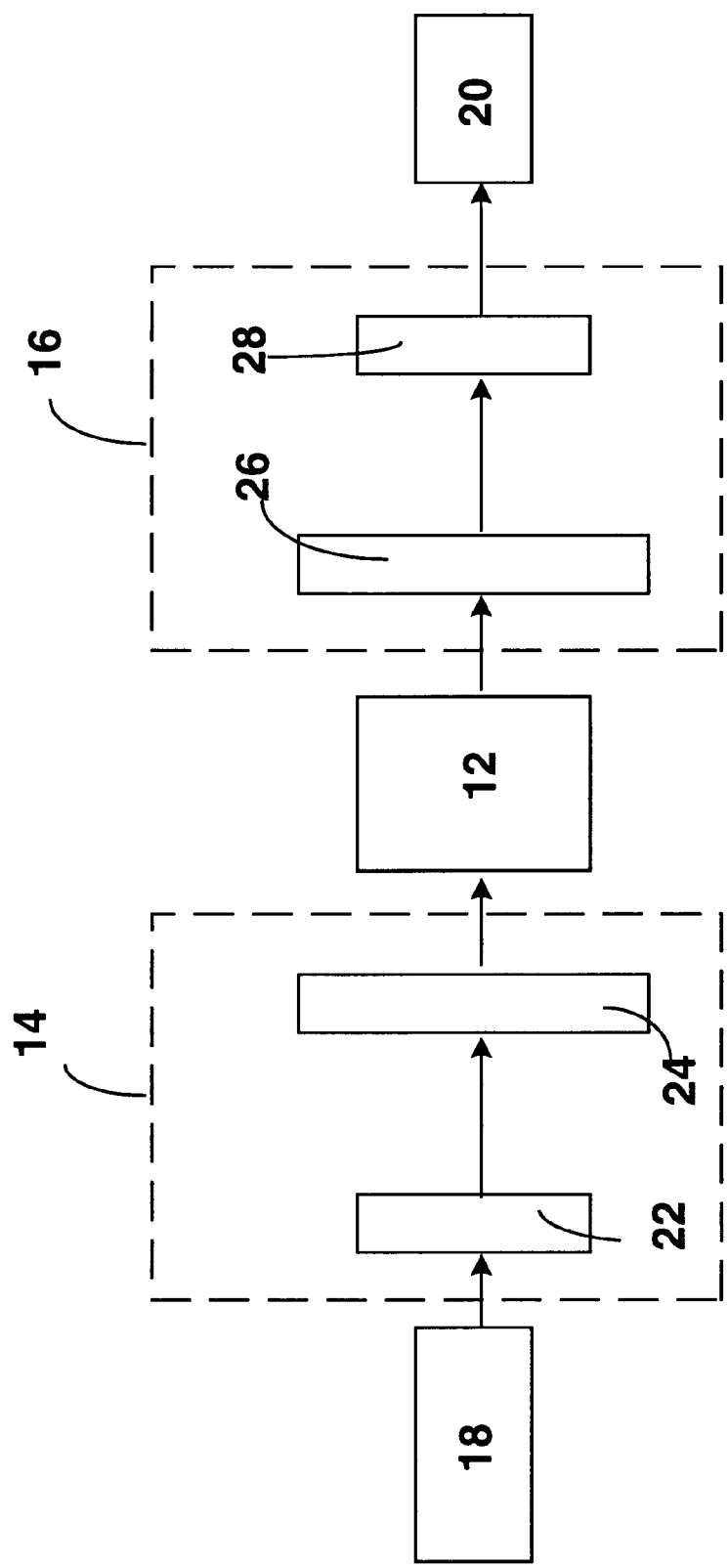
FIG. 2 shows another prior art system for obtaining birefringence of a material.
Figure 3:
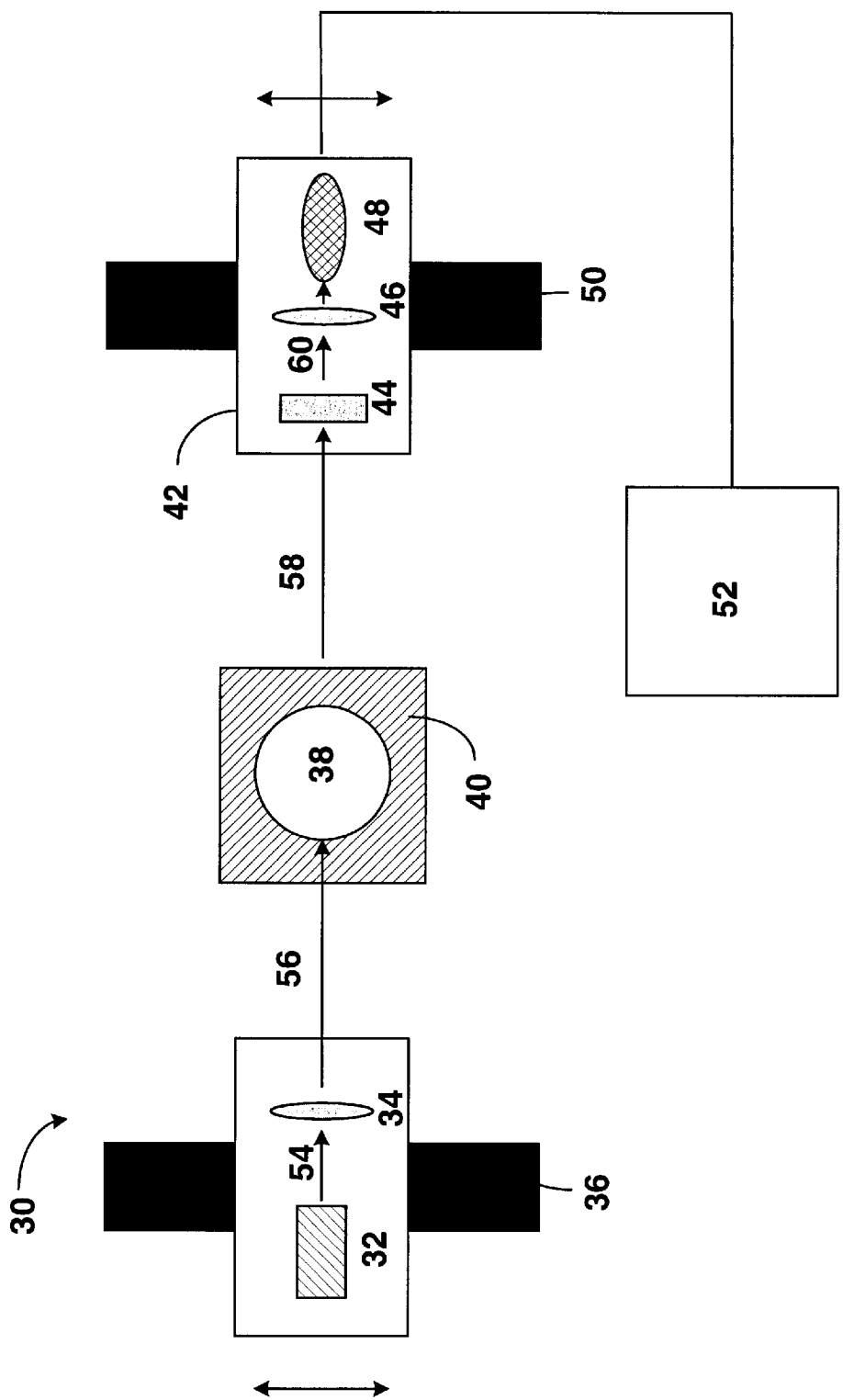
FIG. 3 is a schematic of an automated system for measuring an optical property.

FIG. 3 illustrates an automated system 30 for measuring an optical property, e.g. birefringence, across a sample. The automated system 30 includes a light source unit 32 and a first polarizer 34. The first polarizer 34 may be one made by Corning Inc., sold under the trade name Polarcor®. This type of polarizer creates linear polarized light and has a higher light extinction ratio ($<10^{-5}$) than commonly used sheet polarizers, which have extinction ratios of about ($10^{-4}$). However, the invention is not limited to this type of polarizer. Sheet polarizer or other types of polarizers, e.g., calcite polarizers, can also be used. The light source unit 32 and the first polarizer 34 are mounted on a vertically movable first translational stage 36. The first translational stage 36 preferably has the ability to accurately move as little as 1 micron. Translational stages which can be used with the automated system 30 are commercially available and can be purchased, for example, from Newport Company (model # MTMCC1).

The automated system 30 further includes a detector end 42. The detector end 42 comprises a quarter-wave plate 44, a second polarizer or analyzer 46 oriented in a crossed Nicols fashion with respect to the first polarizer 34, and a photomultiplier 48. The second polarizer or analyzer 46 may be one made by Corning Inc., sold under the trade name Polarcor®, or may be other type of polarizer. The wave plate 44 is not limited to quarter-wave plates, but may be a half-wave plate, for example. The detector end 42 is mounted on a second translational stage 50. The second translational stage 50 can move simultaneously with the first translational stage 36, while keeping the light source unit 32 and the detector end 42 optically aligned. The translational stages 36 and 50 may also move independently of one another along a selected line. The analyzer 46 is mounted in a rotation stage (not shown) which is also mounted on the second translational stage 50. The rotation stage has the ability to rotate the analyzer 46 such that the angular position of light extinction can be measured.

The automated system 30 also includes a sample holder 40. In the illustrated embodiment, the sample holder 40 is rotatable and comprises a series of plates with rings (not shown) for holding a sample of a selected shape, e.g., sample 38. The sample holder 40 further comprises a controllable means (not shown) for rotating the sample 38 preferably around a full circle. In the illustrated embodiment, the sample 38 is a birefringent lens blank which has parallel surfaces. It should be understood that the sample 38 can be any shape or material of a birefringent nature, as long as it can be placed physically in the sample holder 40 and can be rotated.

In operation, a light beam 54 from the light source unit 32 enters the polarizer 34. The light beam in this embodiment is a He-Ne laser beam with a wavelength of 632.8 nanometers, but may be any other type of light beam. A planar polarized light 56 emerges from the first polarizer 34 and enters the sample 38. Because of the birefringent nature of the sample 40, when the planar polarized light 56 enters the sample 38, it splits into two light rays (not shown). The two light rays (not shown) recombine into an elliptically polarized light 58 upon exiting from the sample 38. The elliptical polarization of the light 58 is caused by the phase difference between the two light rays.

The elliptically polarized light 58 then enters the quarter-wave plate 44, where it is converted into a linearly or nearly linearly polarized ray 60. This ray 60 then enters the analyzer 46, which is arranged in a crossed Nicols fashion with respect to the first polarizer 34. The light beam emerging from the analyzer 46 then enters a photomultiplier 48, which measures the light intensity. The results are analyzed by a computer 52. By measuring the angular position at which the light is extinguished as it passes through the two crossed linear polarizers 34 and 46, the birefringence at a particular point in the sample 38 can be determined. The angular position at which the light is extinguished is obtained by rotating the second polarizer or analyzer 46, with respect to the first linear polarizer 34, until the light intensity measured by the photomultiplier 48 diminishes to some minimum value, e.g., zero. The translation stages 36 and 50 are then moved vertically, and the process is repeated until a linear series of points at a particular angular orientation of the sample 38 has been taken. The sample 38 is then rotated through a predetermined angle to the next desired measurement location, and the process is repeated.

Data points are sampled by a process which takes parameters, e.g., sample thickness, sample diameter, spatial resolution, entered by a user and uses these parameters to determine the coordinates of all data points lying within the sample coordinate system. The computer 52, based on the parameters entered by the user, calculates the geometric center of the sample 38. There is no restriction on the shape of the sample 38 because determination of the geometric center of the sample is a mathematical construct. The geometric center of the sample 38 is used as the origin of a Cartesian coordinate system. The process works by first converting the desired measurement locations on the sample 38 from Cartesian coordinates to polar coordinates. The process then transforms these polar coordinates into command signals. The process may also work directly with the Cartesian coordinates.

Figure 4:
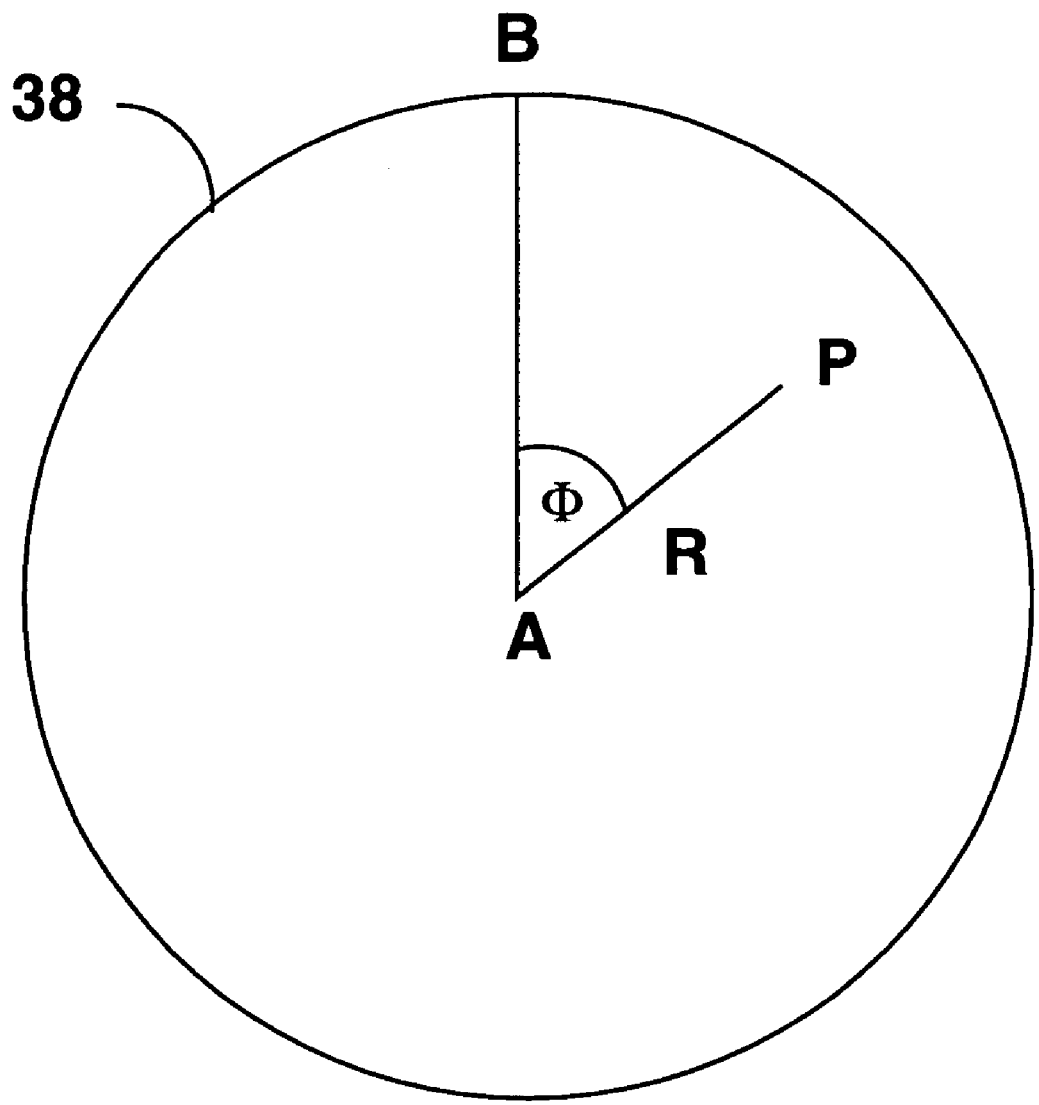
FIG. 4 illustrates birefringence measurement at a point on a sample.

The command signals automatically rotate the sample holder 40 to the appropriate orientation and move the translational stages 36 and 50 to the appropriate height so that birefringence measurements can be made at the desired measurement locations on the sample 38. As illustrated in FIG. 4, birefringence may be measured at a data point P on the sample 38 by rotating the sample 38 through Φ degrees so that the data point P lies within the measurement region, i.e., along line segment AB. The translational stages 36 and 50 may then be moved so that the light source unit 32 and the detector end 42 are aligned with the data point P. If the light source unit 32 and the detector end 42 are initially aligned with the center A of the sample 38, the translational stages 36 and 50 will be moved R units. This process may be repeated for all measurement locations on the sample 38 until the system completely maps the birefringence of the sample.

Alternatively, the computer 52 can be programmed to rotate the sample holder 40 and correspondingly move the translational stages 36 and 50 to make measurements along a substantially spiral pattern about the cross-section of the sample 38. In one example, the amount of angular rotation of the sample holder 40 between successive measurement points can be related to the lateral position of the stages 36 and 50 with respect to the center of the sample 38, so that substantially constant spatial resolution of measurement can be maintained.

When the translational stages 36 and 50 and the sample 38 are at the appropriate height and orientation, respectively, the analyzer 46 is rotated to measure birefringence. The birefringence measurement is recorded and stored on the computer 52, where the user can either examine it as the measurement is made or view a summary after all the measurements are taken. The translational stages 36 and 50 can be moved, while keeping the sample 38 in the same orientation, so that birefringence measurements can be made along a line extending from the center of the sample 38. When the translational stages 36 and 50 reach the edge of the sample 38, the sample 38 can be rotated a predetermined amount and the translational stages 36 and 50 can be moved accordingly to allow measurement at the next measurement location.

The process thus described provides advantages in that a single operator can quickly and accurately create a birefringence map of a sample. The process can also eliminate much of the inaccuracy in measuring birefringence manually.

While the example embodiment described herein is directed to measurement of the birefringence of a sample, it should be clearly understood that the automated system can measure other types of optical properties, e.g., transmission. The process described above can easily be extended to other measurements, simply by changing some of the elements, the analyzer or light source. It is also possible to perform continuous measurements while keeping spatial resolution constant, which is previously unknown in the prior art. Also, the process can be extended to look at any optical property in which there is a source and a detector. Specifically, the process applies to any property that measures the state of the energy entering a sample and compares it to the state of the energy leaving a sample.

Those skilled in the art will appreciate that other embodiments of the invention can be devised which do not depart from the spirit of the invention as disclosed herein. Accordingly, the scope of the invention should be limited only by the attached claims.

What is claimed is:

1. An apparatus for measuring an optical property of a sample, comprising:
    a first stage movable along a predetermined line and having a light source mounted thereon;
    a second stage for holding the sample and rotating the sample to a selected angular position;
    a third stage movable along a predetermined line and having a light detector mounted thereon; and
    a controller for coordinating movement of the first stage, the second stage, and the third stage such that the light source, the sample, and the light detector are optically aligned.

2. The apparatus as defined in claim 1, wherein the controller operates the stages to measure the optical property in a predetermined pattern.

3. The apparatus as defined in claim 1, wherein the first and third stages move substantially simultaneously along their respective predetermined lines.

4. The apparatus as defined in claim 1, wherein the controller computes the geometric center of the sample and calculates an increment of movement of the stages.

5. The apparatus as defined in claim 1, wherein the light source comprises a helium-neon laser the first stage further comprises a first linear polarizer.

6. The apparatus as defined in claim 1, wherein the light detector comprises a quarter-wave plate and a second linear polarizer, the second linear polarizer mounted in a rotation stage and oriented at 90 degrees from an orientation of the first linear polarizer.

7. The apparatus as defined in claim 6, further comprising means for rotating the second polarizer and means for measuring an angle of rotation of the second polarizer for determining a birefringence of the sample.

8. The apparatus as in claim 1, wherein the controller is programmed to operate the stages to make measurements in substantially a spiral pattern about a cross-section of the sample.

9. The apparatus as defined in claim 1, wherein the light source comprises a helium-neon laser having a wavelength of 632.8 nm.

10. A method for making automated measurements of an optical property of a sample, comprising:
    moving a first stage supporting a light source and a third stage supporting a light detector to a predetermined position;
    moving a second stage supporting the sample to rotate the sample to a predetermined angular position;
    measuring the optical property of the sample; and
    repeating moving the stages and measuring the optical property of the sample at spaced apart positions along a line until an edge of the sample is reached.

11. The method as defined in claim 10, further comprising calculating the geometric center of the sample and determining a measurement pattern originating at the center.

12. A method for making automated measurements of an optical property of a sample, comprising:
    moving a first stage supporting a light source along a line;
    moving a second stage supporting the sample;
    moving a third stage supporting a light detector along a corresponding line;
    measuring the optical property of the sample with the light source and light detector to provide a plurality of optical property measurements;
    wherein moving the second stage comprises angular rotation by an amount related to a position of the first, third stages relative to a center of the sample.

13. The method as claimed in claim 12, wherein the measurements result in a spiral pattern having constant distance between points.

* * * * *